United States Patent [19]
Berndt

[11] Patent Number: 5,422,720
[45] Date of Patent: Jun. 6, 1995

[54] BLOOD CULTURE SENSOR STATION UTILIZING TWO DISTINCT LIGHT SOURCES

[75] Inventor: Klaus W. Berndt, Stewartstown, Pa.

[73] Assignee: Becton Dickinson and Company, Franklin Lakes, N.J.

[21] Appl. No.: 95,625

[22] Filed: Jul. 21, 1993

[51] Int. Cl.⁶ .................. G01N 21/15; G01N 33/48
[52] U.S. Cl. .................. 356/343; 356/39; 356/341
[58] Field of Search .......... 356/39, 341, 343, 434, 356/435

[56] References Cited

U.S. PATENT DOCUMENTS

| | | | |
|---|---|---|---|
| 3,910,701 | 10/1975 | Henderson et al. | 356/434 |
| 5,059,394 | 10/1991 | Phillips et al. | 356/39 |
| 5,164,796 | 11/1992 | DiGuiseppi et al. | 356/445 |
| 5,293,210 | 3/1994 | Berndt | 356/39 |

*Primary Examiner*—Richard A. Rosenberger
*Attorney, Agent, or Firm*—Alan W. Fiedler

[57] ABSTRACT

A method for determining whether a particular sample vial has bacterial growth includes the steps of introducing a first light into the sample vial and measuring the intensity of the reemerging light. One then introduces a second light which is different from the first light and has either a different wavelength, or is introduced at a different location than the first light. The reemerging intensity from the second light is also measured. A ratio quantity is calculated based on the two reemerging intensities, and the calculated ratio is compared to expected ratios for both positive and negative samples. It has been found that a comparison of the reemerging light intensities provides a very good indication of whether a particular sample is a positive or negative sample. Various methods and formulas for calculating the ratios may be utilized. Graphs associated with the particular methods and formulas are developed experimentally to allow one to compare a particular calculated ratio value to expected values for positive and negative cultures.

19 Claims, 4 Drawing Sheets

BLOOD CULTURE SENSOR STATION UTILIZING TWO DISTINCT LIGHT SOURCES

BACKGROUND OF THE INVENTION

This application relates to a blood culture sensor station which directs two sources of light into a blood culture specimen, measures the reemerging light from both light sources, calculates a ratio based on the two reemerging lights, and determines whether the specimen includes bacteria based on the calculated ratio.

Typically, the presence of bacteria in a patient's body fluid is determined by injecting a small quantity of body fluid (usually blood) into a vial which contains a culture medium. Various types of instruments are utilized to monitor changes in the carbon dioxide content of the vial. Carbon dioxide is a metabolic by-product of bacteria growth, and thus an increase in carbon dioxide in the vial indicates the presence of bacteria in the patient's body fluid.

Sensors have typically been inserted into the vial to test the carbon dioxide content. These so-called invasive sensors are somewhat undesirable due to the risk of cross-contamination. Non-invasive sensor systems have been developed which utilize chemical sensors disposed inside the vial. Typically, such sensors respond to changes in the carbon dioxide concentration by changing color, or by changing their fluorescent intensity. To monitor changes in the known chemical sensors, the systems have typically required one light source, one spectral exitation filter, one emission filter and one photodetector arranged adjacent to each vial. Each of these components must have extremely narrow specification tolerances to avoid substantial station to station sensitivity variations. However, even if it were possible to equalize all of the vial stations, certain lot-to-lot variations in the chemical sensor composition and certain vial-to-vial geometry variations may remain. Thus, the accuracy of such system is sometimes in question.

Some disadvantages of intensity based sensors can be overcome by utilizing fluorescent sensors which change fluorescent lifetime with changing pH, carbon dioxide concentrations, oxygen concentration, or other parameters. Such fluorescent lifetime sensors typically require expensive equipment. Further, color changing or fluorescent chemical sensors have typically required a certain temperature adaption time before a first vial test can be performed. Thus, a test cannot be made immediately upon receiving a vial when utilizing known chemical sensors.

It has been proposed to direct a light source into a vial, and monitor the reemerging light over time. It has been shown that increased carbon dioxide in a specimen will affect the reemerging light. The reemerging light can be evaluated to make a prediction as to the presence of bacterial growth in the vial. Problems remain with such proposed methods. If there is an unusually large amount of specimen within the vial, the medium within the vial may be more opaque than with a lesser amount of specimen. This would in turn effect the reemerging light. For that reason with known light based sensor systems, the amount of specimen within the vial can vary the accuracy of the test. Further, such light based systems do not allow immediate testing upon receipt of a vial.

SUMMARY OF THE INVENTION

In a disclosed method for evaluating a body fluid sample in a culture vial, one calculates a ratio based on the reemerging light intensity from two distinct light sources and compares the calculated ratio to expected ratios for positive and negative culture vials. In this way, one can make a quick evaluation of whether a particular vial is positive. Since one calculates a ratio based on the two reemerging light intensities, variation in the reemerging light due to variations in the amount of specimen in the vial should be cancelled out.

In one disclosed embodiment of the present invention, a first light source having a first set of characteristics is directed into the vial and the reemerging light is monitored at a second position. Light having a second set of characteristics is then directed into the vial, and the reemerging light is again measured at the second position. A "ratio" based on the reemerging light intensity from the first and second light sources is determined and compared to a graph which has been developed experimentally utilizing control positive and negative samples. The term "ratio" has been placed in quotes since the invention preferably does not use a simple ratio of the reemerging lights. Rather, in one method, background light and input light are all included in a formula to calculate the "ratio" quantity. In a second method the reemerging lights are monitored and the intensity of the second light source is adjusted until equal reemerging intensities are measured. A ratio of the intensities of the first and second light source is then calculated. It has been found that a calculated "ratio" using either method provides a very good indication of whether a particular vial is a positive vial containing bacterial growth.

The term "ratio" as utilized in this application is broadly meant to refer to a formula calculated utilizing the measured reemerging light intensities in some way. As stated above, the specific formulas may include other quantities, as in the first example. Moreover, as in the second example, in some formulas there may be no specific calculation using actual measured reemerging intensities. The measured intensities are utilized to reach the adjusted second light intensity quantity which is utilized in the formula. In that sense the second method ratio is "based" on the measured reemerging light intensity.

One main beneficial use of this invention would be to provide an immediate reading of a particular vial upon receipt by a laboratory. It is envisioned that a sensor station according to the present invention would receive all incoming vials for immediate testing to determine whether the particular vial is already positive. If the vial is positive upon arriving at the laboratory, that result can be noted and reported. If the particular vial is not positive upon arrival, the vial may be placed into a "kinetic" system which monitors ongoing bacterial growth within a vial. A vial may become positive, or change to positive over the first 24 hours after the body fluid is injected. Thus, it is possible that a vial which is not immediately positive upon being received by a laboratory could later become positive. Applicant's invention, will identify so-called "delayed" vials which are already positive upon arrival at the laboratory. This will allow health care providers to provide treatment to those patients quicker, and also reduce the number of sample vials which undergo other types of testing to monitor whether they are changing to positive. This invention requires only seconds to complete a test. Other methods take a longer time, and thus it is desirable to reduce the number of vials subjected to the other type of tests.

In one preferred embodiment of this invention, light of a first wavelength is introduced into the vial at a first location. The light intensity introduced $I_1(\lambda_1)$ is measured. The light intensity $I_{12}(\lambda_1)$ reemerging from the vial is measured at a second location. The light of the first wavelength is then turned off, and the background light intensity $I_{02}$ emerging from the second location with no light is then measured. Light of a second wavelength is introduced into the vial from the first location. The intensity introduced $I_1(\lambda_2)$ is measured, and the light intensity $I_{12}(\lambda_2)$ emerging at the second location of the vial from the second light source is also measured. A "ratio" of the two reemerging light intensities is calculated using the following formula:

$$R = \frac{I_{12}(\lambda_1) - I_{02}}{I_{12}(\lambda_2) - I_{02}} * \frac{I_1(\lambda_2)}{I_1(\lambda_1)}$$

In a second mode of operation, the above objective may be achieved by introducing light of a first wavelength fit a first location into the vial, measuring the light intensity $I_{12}(\lambda_1)$ reemerging at the second location on the vial. The light of the first wavelength is turned off, and light of a second wavelength is introduced from the first location. The light intensity $I_{12}(\lambda_2)$ reemerging at the second location due to the second light source is measured. The reemerging intensities $I_{12}(\lambda_1)$ and $I_{12}(\lambda_2)$ from the two light sources are then compared. The intensity of the second light source is adjusted until the reemerging intensities are equal for both light sources. The light intensity $I_1(\lambda_1)$ from the first light source introduced to the vial is measured, as is the adjusted light intensity $I_1(\lambda_2)$ from the second light source. A "ratio" is then calculated as follows:

$$U = \frac{I_1(\lambda_2)}{I_1(\lambda_1)}$$

Although the quantity U is calculated without including any measurement of the reemerging light intensity in the equation, the reemerging intensities are utilized to reach the quantities used in the equation. In that sense, the calculation of U is "based" on measuring the reemerging light intensities.

The second mode of operation is the preferred method, and is advantageous in that there is no measurement of the intensity $I_{02}$ required. Any background light is cancelled out. Also, dark current signals of the photodetector, and sensitivity changes and/or non-linearities of the photodetector at the second location have no impact on the measurement.

It has been found that two effects occur to light passing through a culture medium, absorption and scattering. In aerobic cultures absorption changes are utilized to detect bacterial growth. In anaerobic cultures a change in scattering is the major effect.

The above formulas have been found experimentally to be particularly advantageous when used with aerobic culture media. It has been found that when the calculated ratio quantities R or U are plotted on a graph, measuring the ratio against the volume of specimen in the vial, there is a clear difference between positive and negative samples. Thus, when one reaches a calculated R or U value, one can compare that value to a previously prepared graph and make an accurate prediction as to whether the particular specimen is a positive or a negative. For an aerobic vial the use of the different wavelengths is most advantageous, since the main effect on the reemerging light intensity in the aerobic medium is a wavelength dependent absorption change.

For anaerobic culture vials, it has been found that a somewhat different method is particularly advantageous. In the preferred anaerobic method, light of a third wavelength is introduced at a third location. The intensity of the entering light $I_3(\lambda_3)$ is measured, and the light intensity $I_{34}(\lambda_3)$ reemerging at a fourth location is measured. The third light source is then turned off, and the background light intensity $I_{04}$ reemerging at the fourth location with no light is measured. Light of the third wavelength is then introduced at a fifth location of the vial. The intensity of the entering light $I_5(\lambda_3)$, and the light intensity $I_{54}(\lambda_3)$ reemerging from the fourth location are measured. The "ratio" S is then calculated:

$$S = \frac{I_{54}(\lambda_3) - I_{04}}{I_{34}(\lambda_3) - I_{04}} * \frac{I_3(\lambda_3)}{I_5(\lambda_3)}$$

A second method for anaerobic cultures can also be utilized by introducing light of the third wavelength at the third location into the vial, measuring the light intensity reemerging at a fourth location $I_{34}(\lambda_3)$, turning off the light at the third location, introducing light of the third wavelength at a fifth location and measuring the light intensity $I_{54}(\lambda_3)$ reemerging at the fourth location on the vial. The reemerging intensities $I_{34}(\lambda_3)$ and $I_{54}(\lambda_3)$, are then compared and the intensity introduced at the fifth location is adjusted until the light reemerging intensities are equal. The light intensity $I_3(\lambda_3)$ introduced at the third location, and the adjusted light intensity $I_5(\lambda_3)$ introduced at the fifth location are measured. The ratio quantity W is then calculated;

$$W = \frac{I_3(\lambda_3)}{I_5(\lambda_3)}$$

The use of the different points of introduction for the light source in the anaerobic method is most advantageous since the main effect on the light by the anaerobic medium is scattering.

In summary, it has been found that by introducing two different sources of light with two different sets of characteristics, and comparing the reemerging values some prediction as to whether a particular culture vial is a positive or a negative can be made. It has been found that by varying the wavelength between the two light sources one can make an accurate prediction with regard to aerobic cultures. By varying the point of introduction of the light sources, one can make an accurate prediction of anaerobic cultures.

These and other features of the present invention can be best understood from the following specification and drawings, of which the following is a brief description.

DESCRIPTION OF THE PREFERRED EMBODIMENT

Figure 1:
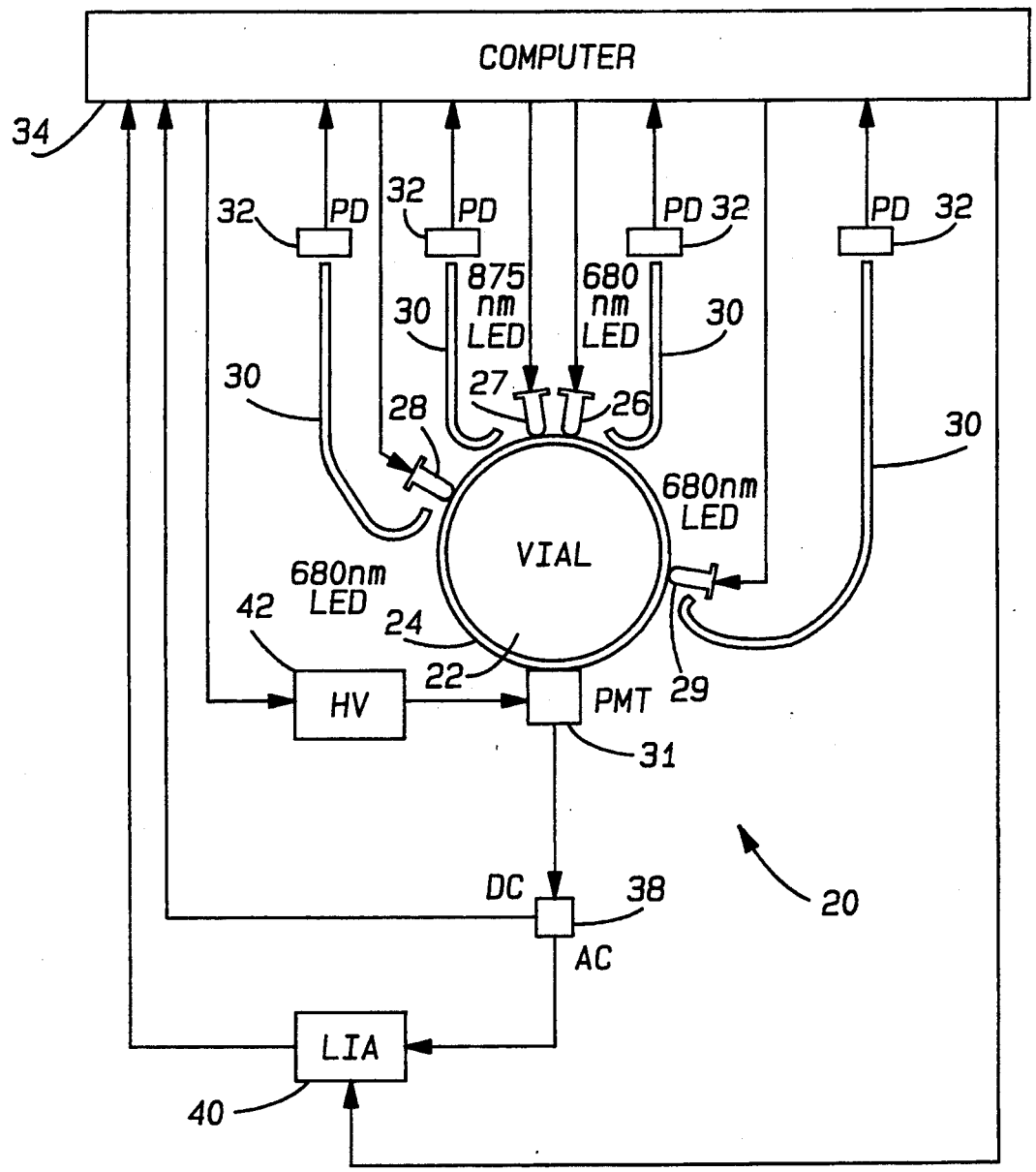
FIG. 1 is a schematic view of a sensor station according to the present invention.

A non-invasive blood culture sensor station 20 for testing a blood sample within a vial 22 is illustrated in FIG. 1. Vial 22 is held within a holding structure 24.

First and second light sources 26 and 27 are positioned at approximately the same location adjacent the vial 22. A third light source 28 and a fourth light source 29 are spaced from the location of sources 26 and 27. A light sensor 31, which is preferably a photomultiplier, is used as the high-sensitivity photodetector. Preferably sources 26, 27, 28 and 29 and sensor 31 are positioned immediately adjacent to vial 22, and most preferably in contact with the vial. In a preferred embodiment, sources 26, 27, 28, and 29, and light sensor 31 are arranged adjacent to the cylindrical vial wall, all at the same distance from the vial bottom. In order to describe the location of the sources relative to the location of the light sensor, we use angles along the vial circumference. It has to be emphasized, however, that these angles are by no means "emission or observation angles" as used in light scattering experiments. Rather, the positioning of the lights and sensors is selected to emphasize the effects on the reemerging light such that the ratios finally calculated provide a good indication of the presence of bacterial activity. In the embodiment shown in FIG. 1, sources 26 and 27 are preferably located at an "angle of 180°" relative to the light sensor 31. Preferably, source 29 is spaced from sensor 31 by an angle between 45° to 100°, with 85° being preferred. Further, source 28 is preferably spaced from sensor 31 by an angle 100° to 180°, with 135° being preferred. The light sources are preferably LEDs. However, the positions of these light sources is more exemplary. For example, sources 26 and 27 do not need to be located at the same location.

A portion of the light being introduced from sources 26, 27, 28 and 29 is guided from the light sources into an optical fiber 30, and through each optical fiber 30 into an input source monitor photodetector 32. All four photodetectors 32 are connected to a computer 34 which controls the entire station 20. A known computer may be utilized. As shown, computer 34 also controls the power to light sources 26, 27, 28 and 29.

Sensor 31 is connected to an AC/DC splitter 38, with the DC output of the splitter 38 connected to computer 34. Computer 34 controls the high voltage power supply 42 for sensor 31 so that approximately the same DC photocurrent level is generated, independent of the amount of blood in the vial 22.

The AC output of splitter 38 is connected to a lock-in amplifier 40, which receives a reference signal from computer 34. The output of the lock-in amplifier 40 is fed to computer 34.

When used to test an aerobic culture vial, light sources 26 and 27 are utilized. Preferably, source 26 is operated with light having a wavelength of 500–800 nm. Most preferably light source 26 is operated at a wavelength of 680 nm. Light source 27 is preferably operated with a wavelength of 805–1500 nm. Preferably, the wavelength of second source 27 is set at 875 nm. It is preferred that a minimum difference of at least 100 nm be maintained between the wavelengths of sources 26 and 27.

The first and second light sources 26 and 27 are turned on and off in a periodic alternating mode, and the sensor 31 measures the intensity of the light reemerging from vial 22. In a most preferred embodiment of this invention, the lock-in amplifier output signal is utilized within computer 34 to control the intensity of second light source 27 by adjusting that intensity until the first and second light sources 26 and 27 cause identical intensities to be measured by sensor 31. Once this condition is reached, the lock-in amplifier output signal is equal to 0.

The intensity introduced by the first light source 26, and the adjusted intensity from the second light source 27 are measured through their respective fibers 30 and photodetector 32. A ratio of those two intensities is calculated using the formula for U set forth above.

As an alternative to calculating the ratio U, the ratio R may be calculated by measuring the other quantities required for such calculations as set forth above.

In operation with anaerobic cultures, the third wavelength is preferably in the range of 500–1500 nm, with 680 nm being a preferred wavelength. Preferably the system is operated to vary the intensity of the light introduced at either the third or fourth light source 28 and 29 until the measured intensities are equal. The intensities introduced from sources 28 and 29 are measured and computer 34 calculates the quantity W by the equation set forth above. Again, as an alternative to calculating the ratio W, one may also calculate the ratio quantity S according to the formula set forth above. It has been found that the calculated quantities or "ratios" show a clear distinction between a positive and negative sample vial.

Figure 2:
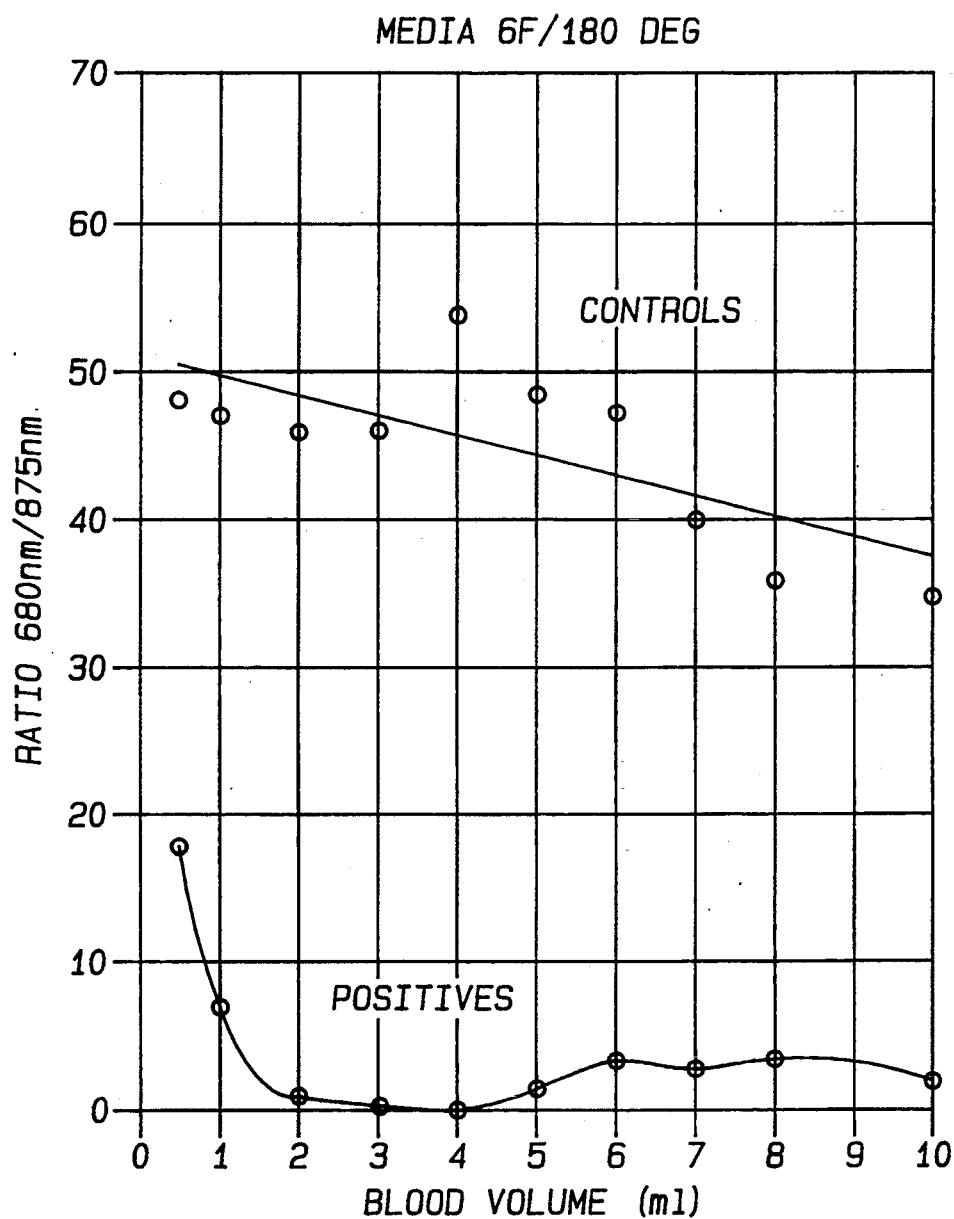
FIG. 2 is a graph showing a calculated "ratio" vs. blood volume for a particular type of aerobic culture.

FIG. 2 is a graph plotting the ratios R or U (these two values should normally be identical, although they are calculated using different formulas) vs. the blood volume in a sample vial. This graph was prepared from tests on standard vials containing negative controls, and other standard vials containing bacteria. As shown, the negative controls have ratios of above 30, and up to 50, depending on the blood volume. As also shown, all positive controls had values below 20, and typically values below 10.

Given this large distinction between the ratios for positive and negatives, once a calculated ratio has been reached for a particular sample, one will be able to make a good prediction of whether that sample is a positive or a negative by comparing it to a graph prepared experimentally such as that shown in FIG. 2.

Figure 3:
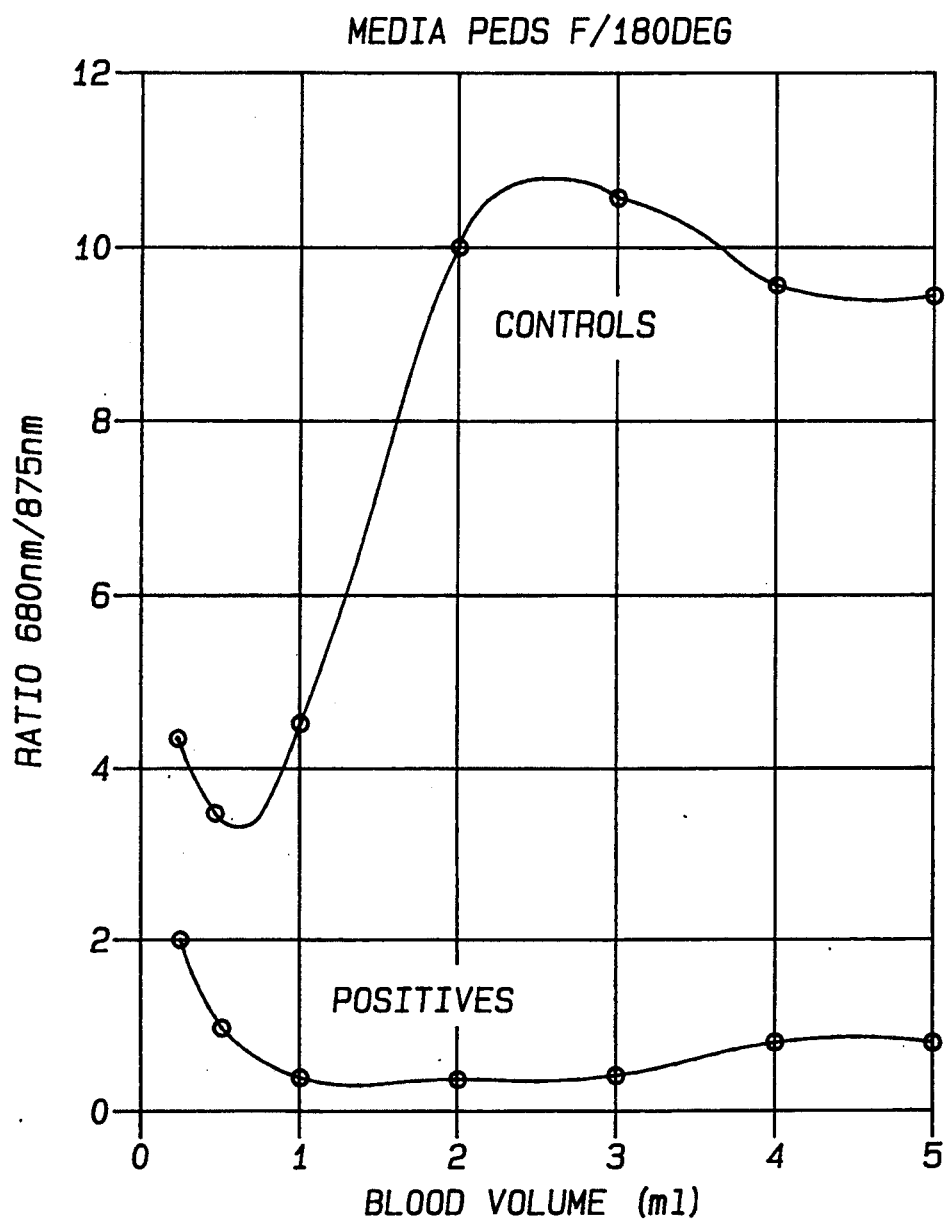
FIG. 3 is a graph showing a calculated "ratio" vs. blood volume for a type of aerobic culture utilized for pediatrics.

FIG. 3 shows a similar graph prepared using a pediatric vial formula. The pediatric vials typically include less blood volume, but still have a large distinction in the ratios between the positive and controls. This is particularly true beyond 1 ml of blood volume.

Figure 4:
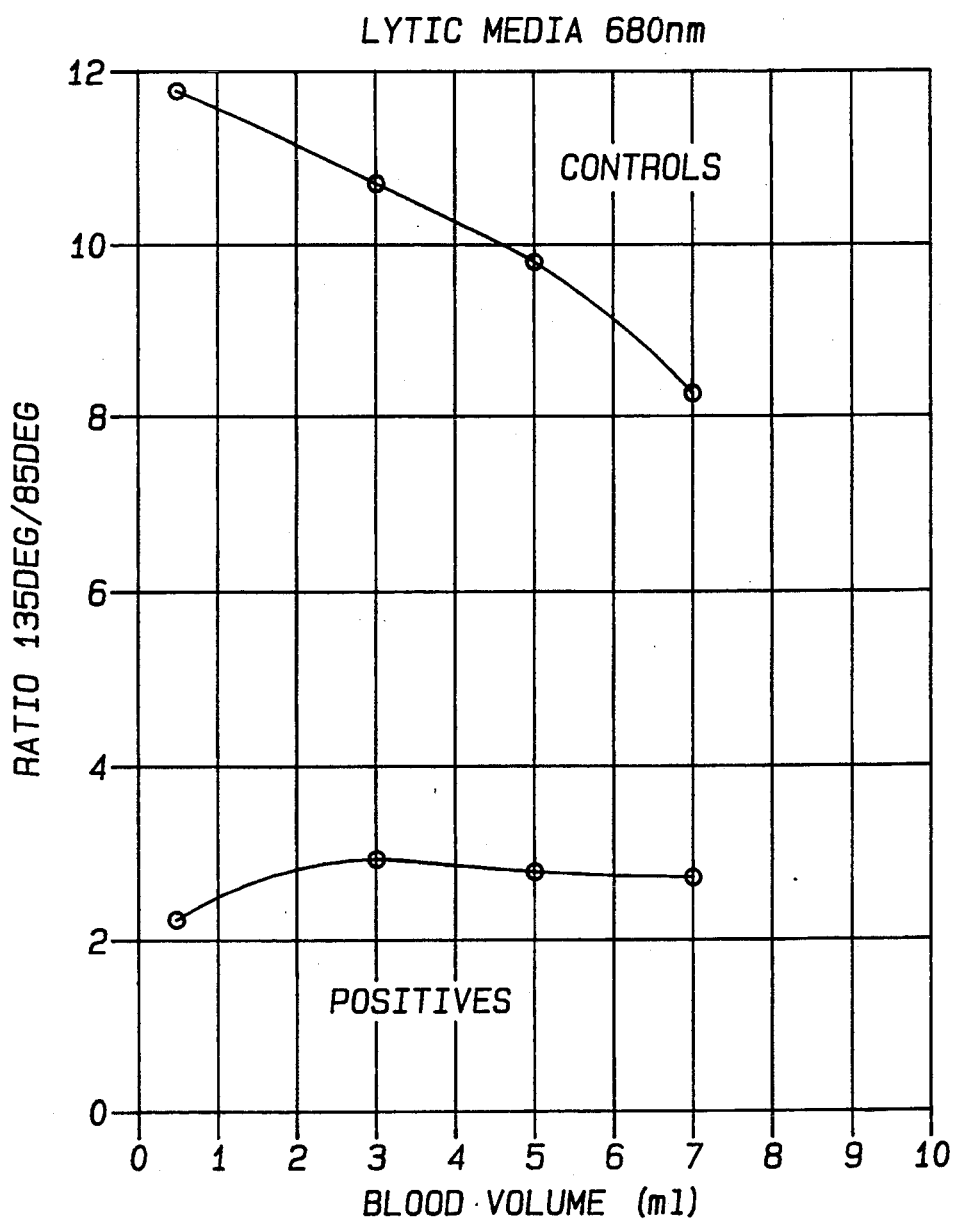
FIG. 4 is a graph showing a calculated "ratio" vs. blood volume for a particular type of anaerobic culture.

FIG. 4 shows experimental results obtained on anaerobic vials, and again shows the differences between the negative and the positive vials. The distinction between the two is clear, with all of the negative controls being above eight, and all of the positive being below three.

In preparing the experimental graph shown in FIG. 2, standard BACTEC TM vials containing a standard BACTEC TM 6F aerobic medium available from Becton Dickinson Diagnostic Instrument Systems in Sparks, Md. were utilized. FIG. 3 was prepared utilizing standard BACTEC TM vials containing a BACTEC TM peds F aerobic medium also available from Becton Dickinson. FIG. 4 was prepared using standard BACTEC™ vials containing a standard BACTEC™ LYTIC anaerobic medium available from Becton Dickenson.

In further modifications of this invention, photodetectors 32 could be replaced by having all four fibers 30 being fed into one photodetector. The photomultiplier sensor 31 could be replaced by a large-area photodiode, followed by a logarithmic amplifier. Further, sensor 31 could be replaced by a large-area photodiode, followed by an adjustable-gain amplifier. With such an option, computer 34 would preferably control the adjustable gain of the amplifier so that approximately the same output signal level is generated independent of the amount of blood in the culture vial. In yet another modification, the lock-in amplifier 40 could be removed with computer 34 taking over the function of the lock-in amplifier. Finally, it is preferred that the sensor station be equipped with a bar code reader to identify a vial, and whether the vial is aerobic or anaerobic, and initiate the appropriate operational mode.

In a most preferred method of utilizing the sensor station 20 according to this invention, a vial 22 is inserted into station 20 for an initial test immediately upon receipt by a laboratory. If that initial test determines that the vial is already positive, such is noted. If the initial test shows that the vial is negative, that vial could be put into another sensor station of the "kinetic" type which makes ongoing measurements. In this way, one would be able to identify "delayed" vials and make an immediate reading of whether the particular vial is positive.

Further, as is shown on the attached graphs, the amount of blood in the vial will not effect the accuracy of the detection method. Although light is the preferred radiation used in this invention, it should be understood that other types of electromagnetic radiation may be used.

A preferred embodiment of this invention has been disclosed, however, a worker of ordinary skill in the art would recognize that certain modifications would come within the scope of this invention. It would be possible, for example, to locate part of the light sources on the side wall, and part of the sources on the vial bottom, or to locate all sources and the light sensor on the vial bottom. It would also be possible to use vials with a non-cylindrical cross-section, and to distribute the sources and the detector over different surface sections. For that reason the following claims should be studied in order to determine the true scope and content of this invention.

What is claimed is:

1. A method of evaluating a body fluid sample comprising the steps of:
   (a) directing a first electromagnetic radiation source into a sample to be tested;
   (b) measuring the intensity of reemerging electromagnetic radiation from the sample due to the first electromagnetic radiation;
   (c) directing a second electromagnetic radiation into the sample;
   (d) measuring the intensity of reemerging electromagnetic radiation from the sample due to the second electromagnetic radiation;
   (e) comparing the reemerging intensities measured during steps (b) and (d);
   (f) modifying the intensity of the radiation directed into the sample during step (c) until the intensity of the reemerging radiation measured at steps (b) and (d) is equal;
   (g) measuring the intensity of the radiation introduced during step (a) and the modified intensity of the radiation being directed into the sample during step (f);
   (h) calculating a ratio of the intensity of the radiation directed into the sample during step (a) and the modified intensity directed into the sample during step (f); and
   (i) comparing the calculated ratio to a predetermined ratio for a sample evidencing bacterial growth and a predetermined ratio for a sample not evidencing bacterial growth to make a determination as to whether the particular sample is evidencing bacterial growth.

2. A method as recited in claim 1, wherein said first and second radiations have different wavelengths.

3. A method as recited in claim 2, wherein said first and second radiations are directed into the sample at approximately a first location.

4. A method as recited in claim 3, wherein the measurements of steps (b), and (d) are performed at a second location spaced approximately 180° from the first location.

5. A method as recited in claim 4, wherein the sample tested is an aerobic blood culture vial.

6. A method as recited in claim 4, wherein the first electromagnetic radiation has a wavelength between 500 nm to 800 nm and the second electromagnetic radiation has a wavelength of between 805 nm and 1500 nm.

7. A method as recited in claim 6, wherein the difference between the wavelengths of the first and second radiations is selected to be at least 100 nm.

8. A method as recited in claim 1, wherein the radiation introduced during steps (a) and (c) is directed into the sample from different locations.

9. A method as recited in claim 8, wherein the radiation introduced during steps (a) and (c) has the same wavelength, and the reemerging radiation is measured during steps (b) and (d) at a single measurement point.

10. A method as recited in claim 9, wherein the different locations are located different distances from the single measurement point where the measurements of steps (b) and (d) are made.

11. A method as recited in claim 10, wherein the tested samples are anaerobic blood samples.

12. A method as recited in claim 8, wherein intensities of the radiations introduced in steps (a) and (c) are measured, as is the background emerging radiation with no radiation being introduced, and are then used to calculate the ratio in step (h) having a value S calculated from the measured radiations as follows:

$$S = \frac{I_{54}(\lambda_3) - I_{04}}{I_{34}(\lambda_3) - I_{04}} \cdot \frac{I_3(\lambda_3)}{I_5(\lambda_3)};$$

wherein $I_{34}(\lambda_3)$ and $I_{54}(\lambda_3)$ are the measured intensities of steps (b) and (d), respectively, $I_3(\lambda_3)$ and $I_5(\lambda_3)$ are the intensities directed into the sample in steps (a) and (c), respectively. $I_{04}$ is the background intensity emerging from the sample; and wherein the calculated value of S is compared to a predetermined value of S for a sample evidencing bacterial growth and a predetermined value of S for a sample not evidencing bacterial growth to make a determination as to whether the tested sample is evidencing bacterial growth.

13. A method as recited in claim 12, wherein the tested sample is an anaerobic blood culture vial.

14. A method as recited in claim 1, wherein intensities of the first and second electromagnetic radiations introduced in steps (a) and (c) are measured, as is the background emerging radiation with no radiation being introduced, and the measured radiations are used to calculate the ratio in step (h), the ratio having a value R calculated utilizing the formula:

$$R = \frac{I_{12}(\lambda_1) - I_{02}}{I_{12}(\lambda_2) - I_{02}} * \frac{I_1(\lambda_2)}{I_1(\lambda_1)};$$

wherein $I_{12}(\lambda_1)$ and $I_{12}(\lambda_2)$ are the measured intensities of steps (b) and (d), respectively, $I_1(\lambda_2)$ and $I_1(\lambda_1)$ are the intensities directed into the sample in steps (c) and (a), respectively, $I_{02}$ is the background intensity emerging from the sample; and wherein the calculated value of R is compared to a predetermined value of R for a sample evidencing bacterial growth and a predetermined value of R for a sample not evidencing bacterial growth to determine whether the particular sample is evidencing bacterial growth.

15. A method as recited in claim 1, including the step of determining whether the sample vial is an aerobic sample or an anaerobic sample, and utilizing different wavelengths for said first and second electromagnetic radiation sources if an aerobic sample is identified and utilizing different introduction locations for said first and second electromagnetic radiation sources should an anaerobic sample be identified.

16. A method as recited in claim 15 wherein different electromagnetic radiation sources are utilized when an aerobic sample is identified from those utilized when an anaerobic sample is identified.

17. A method of determining whether a particular sample contains bacterial growth comprising the steps of:
(a) introducing a first electromagnetic radiation having a first set of characteristics into a sample vial;
(b) measuring radiation reemerging from the sample vial as a result of the radiation introduced in step (a);
(c) introducing a second electromagnetic radiation having a second set of characteristics into the sample vial;
(d) measuring radiation reemerging from the sample vial as a result of the radiation introduced in step (c);
(e) comparing the radiation intensities measured in step (b) and (d), and modifying the intensity of the second electromagnetic radiation until the intensity of the radiation measured in step (d) is equal to the intensity of the radiation measured in step (b); and
(f) measuring the intensity of the radiation introduced in step (a) and the modified intensity of the radiation introduced in step (e), calculating the ratio of those two intensities, and comparing the calculated ratio to a predetermined ratio for a sample evidencing bacterial growth and a predetermined ratio for a sample not evidencing bacterial growth to make a determination as to whether the sample vial is evidencing bacterial growth.

18. A method as recited in claim 17, wherein the first electromagnetic radiation is selected to have a different wavelength than the second electromagnetic radiation.

19. A method as recited in claim 17, wherein the first electromagnetic radiation is introduced into the sample vial at a first location, and the second electromagnetic radiation is introduced into the sample vial at a second location spaced from the first location.

* * * * *